(12) United States Patent
Peng et al.

(10) Patent No.: US 11,353,134 B2
(45) Date of Patent: Jun. 7, 2022

(54) OPERATING STRUCTURE OF PILOT-OPERATED SOLENOID VALVE

(71) Applicant: HARDA (XIAMEN) PLASTIC CO., LTD., Fujian (CN)

(72) Inventors: Kesheng Peng, Xiamen (CN); Yulin Qiu, Xiamen (CN); Shengsen Zhan, Xiamen (CN)

(73) Assignee: HARDA INTELLIGENT TECHNOLOGIES CO., LTD., Fujian (CN)

( * ) Notice: Subject to any disclaimer, the term of this patent is extended or adjusted under 35 U.S.C. 154(b) by 75 days.

(21) Appl. No.: 16/920,734

(22) Filed: Jul. 5, 2020

(65) Prior Publication Data
US 2021/0200248 A1    Jul. 1, 2021

(30) Foreign Application Priority Data

Dec. 27, 2019   (CN) .......................... 201922396594.3

(51) Int. Cl.
| | | |
|---|---|---|
| *F16K 31/06* | (2006.01) | |
| *G01N 33/18* | (2006.01) | |
| *F16K 31/143* | (2006.01) | |
| *G05D 7/06* | (2006.01) | |

(52) U.S. Cl.
CPC ........ *F16K 31/0655* (2013.01); *F16K 31/143* (2013.01); *G01N 33/18* (2013.01); *G05D 7/0635* (2013.01)

(58) Field of Classification Search
CPC .... F16K 31/0655; F16K 31/13; F16K 31/143; F16K 31/145; F16K 31/14; F16K 31/40; F16K 31/42; F16K 31/508; G01N 33/18

USPC ................................................... 251/268, 269
See application file for complete search history.

(56) References Cited

U.S. PATENT DOCUMENTS

| | | | | | |
|---|---|---|---|---|---|
| 178,492 | A | * | 6/1876 | Walter | F16K 41/10 251/268 |
| 682,688 | A | * | 9/1901 | Hart | F16K 41/02 251/214 |
| 912,597 | A | * | 2/1909 | McNeil | E03D 3/06 251/18 |
| 1,398,025 | A | * | 11/1921 | James | F16K 27/07 137/590 |
| 1,614,468 | A | * | 1/1927 | Haas | E03D 3/06 251/18 |
| 1,660,352 | A | * | 2/1928 | Payne | E03D 3/04 137/880 |

(Continued)

*Primary Examiner* — William M McCalister
(74) *Attorney, Agent, or Firm* — Leong C. Lei

(57) ABSTRACT

An operating structure of a pilot-operated solenoid valve is provided. The pilot-operated solenoid valve includes a valve body having a main valve orifice and a pilot valve orifice to open and close the main valve orifice. The pilot valve orifice communicates with an accommodating chamber of the valve body. The operating structure includes a knob, an adjustment rod, and a water stop nut. The knob is positioned and fitted to an opening of the accommodating chamber. The adjustment rod is hermetically fitted in the accommodating chamber. One end of the adjustment rod is threadedly connected to the knob, and the other end of the adjustment rod is connected to the water stop nut. The adjustment rod is driven to move axially by rotation of the knob for driving the water stop nut to control the opening and closing of the main valve orifice.

5 Claims, 5 Drawing Sheets

(56) References Cited

U.S. PATENT DOCUMENTS

| | | | | |
|---|---|---|---|---|
| 2,470,470 A | * | 5/1949 | Carbon | F16K 31/406 251/77 |
| 2,657,005 A | * | 10/1953 | Van | F16K 39/024 251/269 |
| 2,823,007 A | * | 2/1958 | Carr | F16K 31/143 251/269 |
| 3,006,361 A | * | 10/1961 | Reinemann | F16K 43/00 137/454.5 |
| 3,044,489 A | * | 7/1962 | Hs | F16K 27/02 137/556.3 |
| 3,064,674 A | * | 11/1962 | Carfagna | F16K 41/023 137/315.28 |
| 3,082,786 A | * | 3/1963 | McLean | F16K 27/02 137/454.5 |
| 3,770,247 A | * | 11/1973 | Nelson | F16K 39/04 251/282 |
| 3,830,464 A | * | 8/1974 | Parker | F16K 1/02 251/269 |
| 4,024,890 A | * | 5/1977 | Yasuoka | F16K 1/221 137/556.3 |
| 4,027,851 A | * | 6/1977 | Schlotman | F16K 31/508 251/172 |
| 4,064,904 A | * | 12/1977 | Tolnai | F16K 31/508 137/454.5 |
| 4,154,259 A | * | 5/1979 | Ellis | E03B 9/04 137/298 |
| 4,230,300 A | * | 10/1980 | Wiltse | A61M 5/16877 251/205 |
| 4,363,465 A | * | 12/1982 | Morrill | F16K 41/04 137/246.12 |
| 4,368,754 A | * | 1/1983 | Roberts | F16K 27/0245 137/315.13 |
| 4,468,001 A | * | 8/1984 | Stanic | F16K 1/02 137/315.4 |
| 4,501,289 A | * | 2/1985 | Pauliukonis | F16K 11/044 137/315.4 |
| 4,650,152 A | * | 3/1987 | Doutt | B23K 11/3018 251/16 |

\* cited by examiner

OPERATING STRUCTURE OF PILOT-OPERATED SOLENOID VALVE

BACKGROUND OF THE INVENTION

1. Field of the Invention

The present invention relates to a solenoid valve, and more particularly to an operating structure of a pilot-operated solenoid valve.

2. Description of the Prior Art

In a pilot-operated solenoid valve, when energized, a valve stein is lifted by the electromagnetic force of the solenoid valve to open a pilot valve orifice. At this time, the pressure in the upper chamber of the solenoid valve is relieved through a pilot hole, forming a differential pressure around a spool valve. Under the action of the pressure difference, the fluid pressure pushes the spool valve upward to open a main valve orifice. When the power is off, under the action of the spring force and the gravity of the spool valve, the valve stein is returned, the pilot hole is closed, the spool valve is moved downward, and the main valve orifice is closed. The pressure in the upper chamber of the solenoid valve increases, and the fluid pressure pressurizes the spool valve for better sealing.

Pilot-operated solenoid valves are widely used for induction faucets in the bathroom and kitchen as important actuators. However, when in use, in the case of a circuit failure, coil failure, no power supply, etc., the solenoid valve will not be actuated normally, which will cause inconvenience to the user. In view of this, the pilot solenoid valve is provided with a knob as a manual operating structure. The knob is rotated to open and close the pilot hole without energizing to indirectly open and close the main valve orifice. Existing pilot-operated solenoid valves are usually installed under the basin, and the operating space is limited. The knob further increases the difficulty of operation, especially when the knob is turned outward, it will further decrease the operation space, resulting in difficulty in operation.

SUMMARY OF THE INVENTION

The primary object of the present invention is to provide an operating structure of a pilot-operated solenoid valve, which can restrain the knob from being displaced relative to the pilot-operated solenoid valve during rotation, so as to achieve the purpose of simple operation.

In order to achieve the above object, the present invention adopts the following technical solutions:

An operating structure of a pilot-operated solenoid valve is provided. The pilot-operated solenoid valve includes a valve body having a main valve orifice and a pilot valve orifice. Opening and closing of the pilot valve orifice guides opening and closing of the main valve orifice. The valve body is formed with an accommodating chamber. The pilot valve orifice communicates with the accommodating chamber. The operating structure includes a knob, an adjustment rod, and a water stop nut. The knob is positioned and fitted to an opening of the accommodating chamber. The adjustment rod is hermetically fitted in the accommodating chamber. A first end of the adjustment rod is threadedly connected to the knob. A second end of the adjustment rod is connected to the water stop nut. The adjustment rod is movable along an axial direction of the accommodating chamber with rotation of the knob to drive the water stop nut for opening and closing the pilot valve orifice to control the opening and closing of the main valve orifice.

Preferably, the knob has a protruding portion. The protruding portion faces the adjustment rod. The protruding portion is formed with a screw hole for the adjustment rod to be screwed therein. The first end of the adjustment rod is screwed in the screw hole.

Preferably, an annular flange protrudes from the opening of the accommodating chamber toward the knob. The knob is sleeved on the annular flange. The protruding portion is inserted in the annular flange and is positioned by a limiting buckle.

Preferably, the annular flange is formed with an insertion hole for the limiting buckle to be movably fitted therein. The insertion hole passes through an inner wall of the annular flange. An outer periphery of the protruding portion is formed with an insertion groove for the limiting buckle to be fitted therein. The limiting buckle is inserted into the insertion hole and fitted in the insertion groove to restrain the knob from moving in the axial direction of the accommodating chamber.

Preferably, an outer periphery of the adjustment rod is formed with a limiting block. A side wall of the accommodating chamber is formed with a limiting groove. The limiting block is engaged with the liming groove to restrain rotation of the adjustment rod in the accommodating chamber Preferably, at least one sealing ring is sleeved on an outer periphery of the adjustment rod. The sealing ring is movably and hermetically fitted between the outer periphery of the adjustment rod and a side wall of the accommodating chamber.

Preferably, the at least one sealing ring includes two sealing rings.

Preferably, the valve body is provided with a water quality monitoring device for detecting water quality of water passing through the valve body and sending a water quality signal.

After adopting the above technical solutions, the knob of the present invention is rotatably positioned and fitted at the opening of the accommodating chamber. The rotation of the knob drives the adjustment rod to move the water stop nut to open or close the pilot valve orifice, so that the rotation of the knob no longer generates displacement, which is convenient for operation and more suitable for the limited space under the basin. In addition, the present invention does not require a complicated mechanical connecting structure, has a simple structure, is easy to install, is more suitable for the improvement of the existing structures, and reducing the cost of improvement.

In addition, the water quality monitoring device can detect the quality of the water source in real time to ensure the health of users.

DETAILED DESCRIPTION OF THE PREFERRED EMBODIMENTS

Embodiments of the present invention will now be described, by way of example only, with reference to the accompanying drawings.

Figure 1:
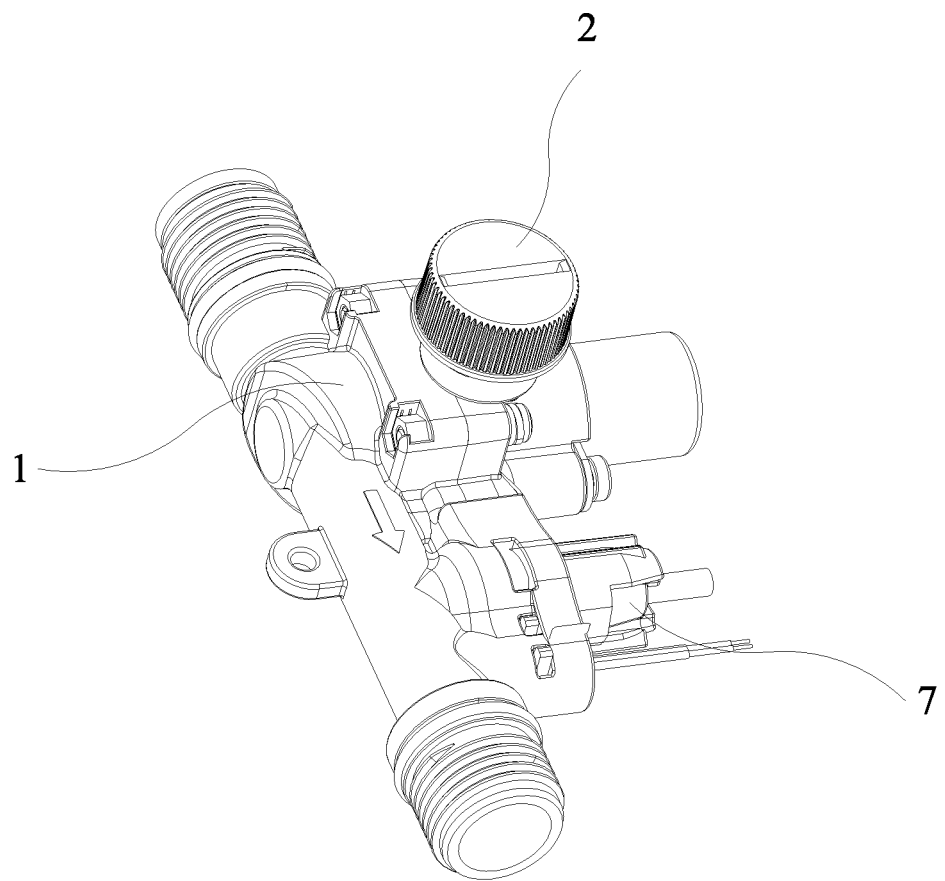
FIG. 1 is a perspective view according to a preferred embodiment of the present invention.
Figure 2:
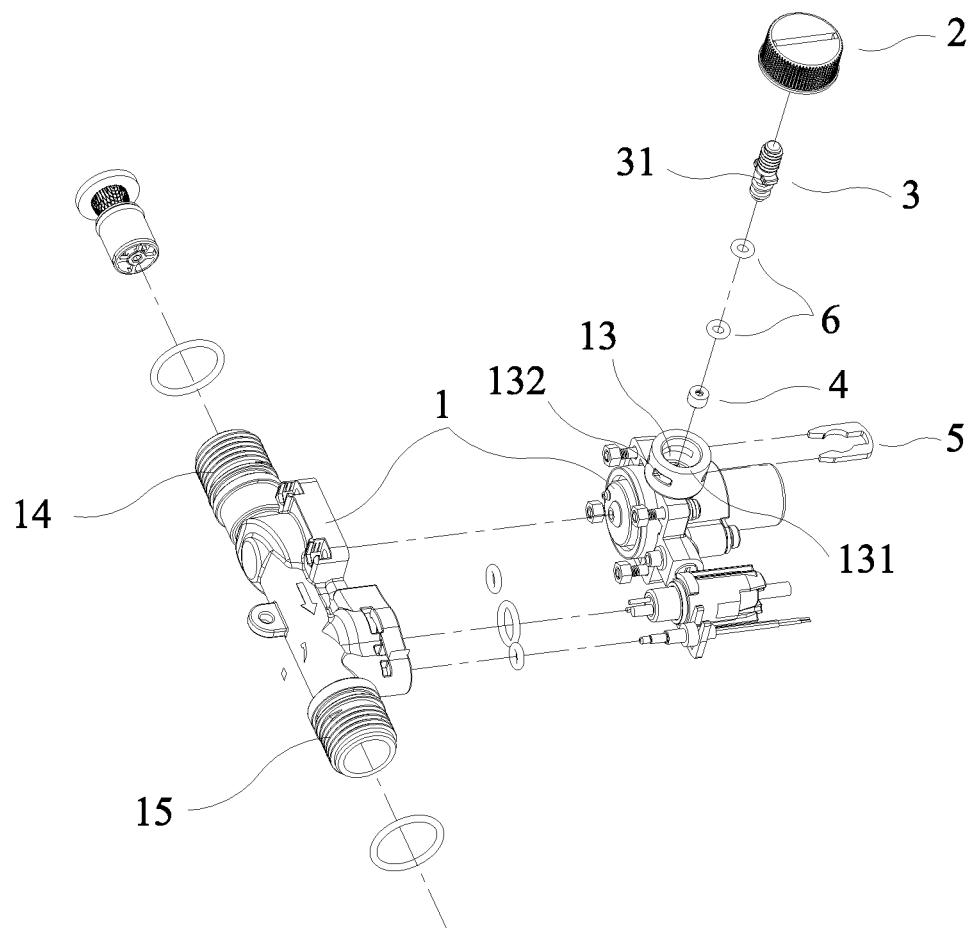
FIG. 2 is an exploded view according to the preferred embodiment of the present invention.
Figure 3:
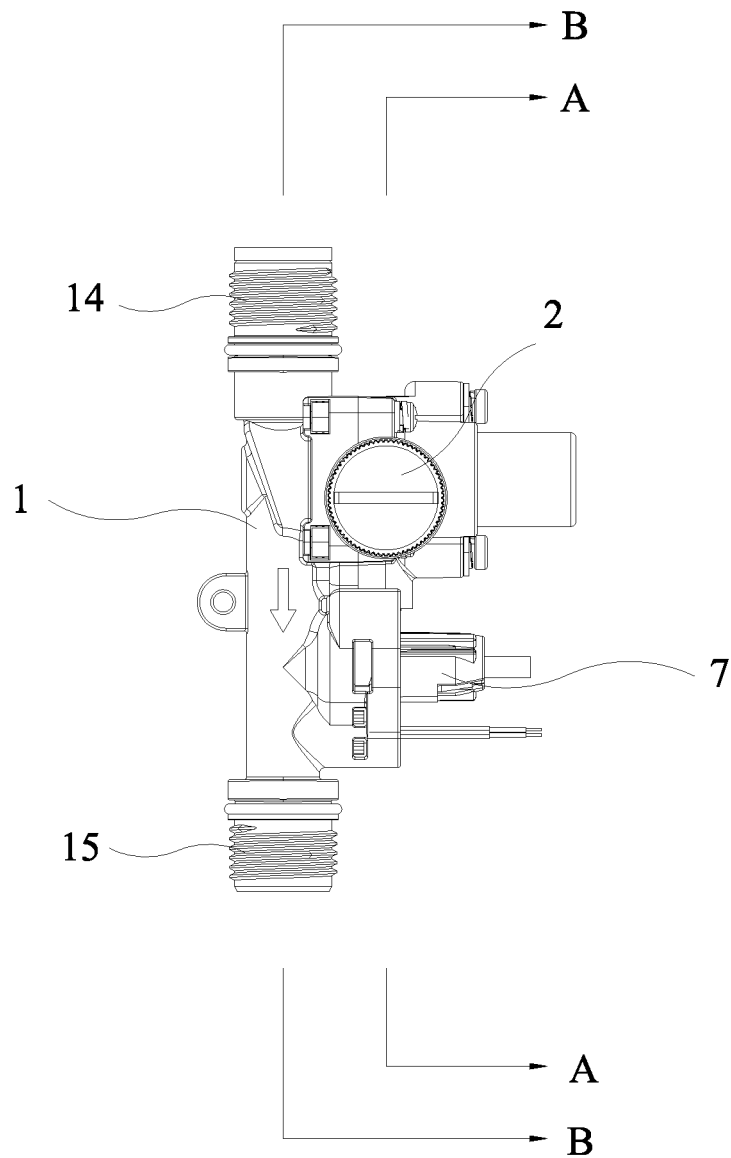
FIG. 3 is a front view according to the preferred embodiment of the present invention.
Figure 4:
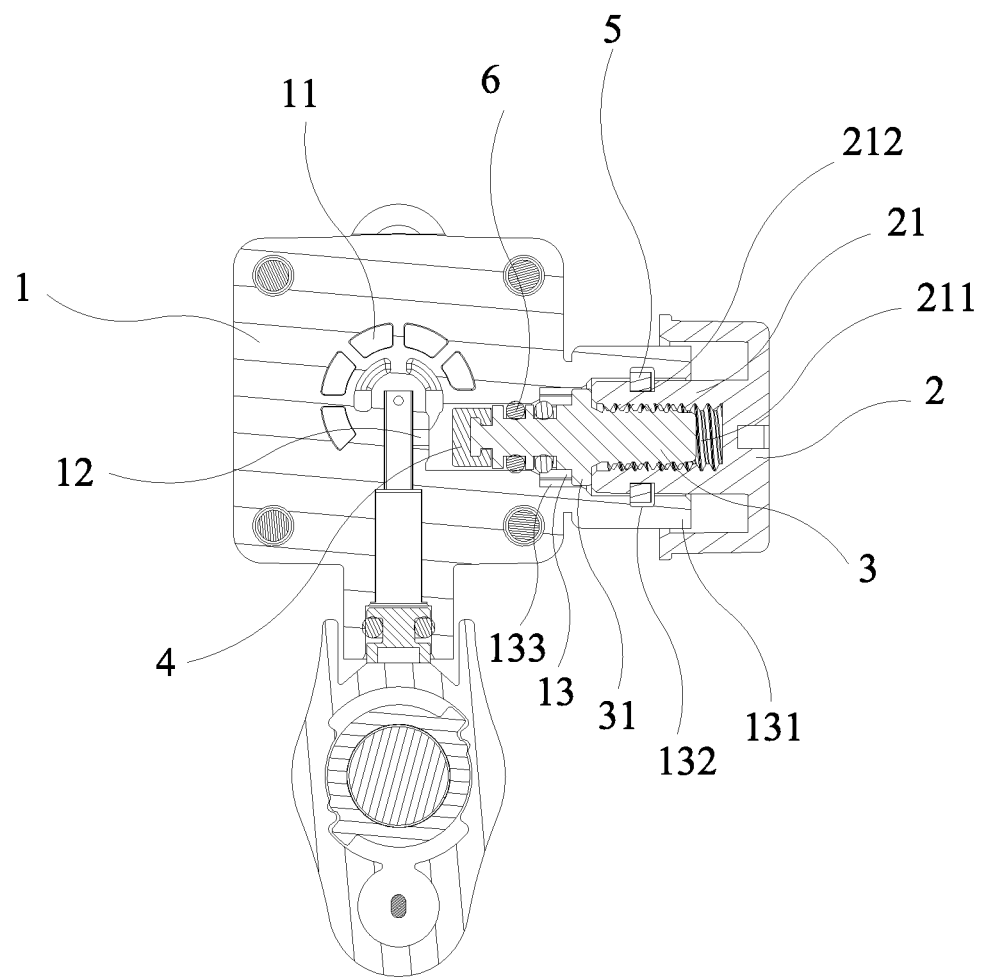
FIG. 4 is a cross-sectional view taken along line A-A of FIG. 3.
Figure 5:
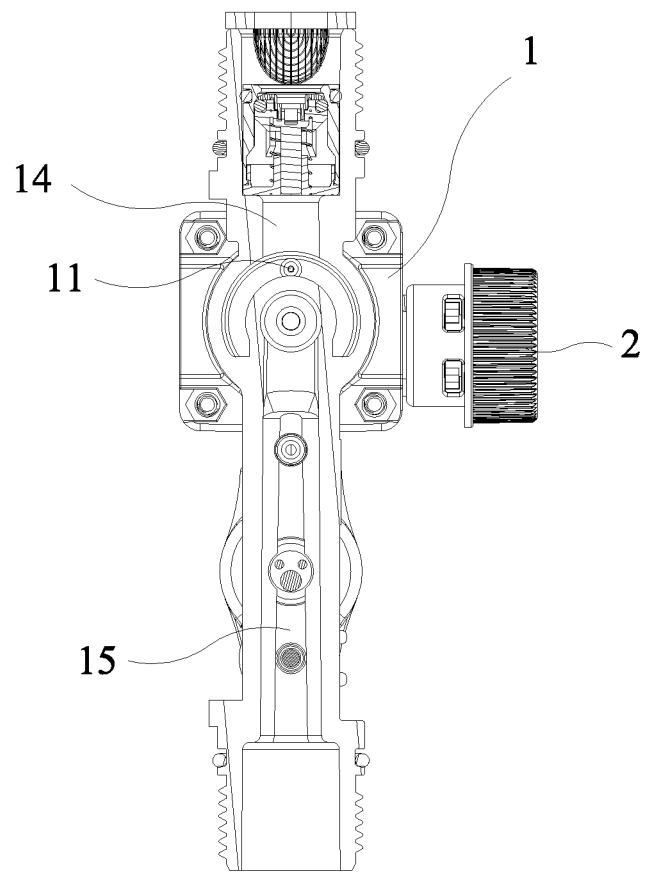
FIG. 5 is a cross-sectional view taken along line B-B of FIG. 3.

As shown in FIG. 1 through FIG. 5, the present invention discloses an operating structure of a pilot-operated solenoid valve. The pilot-operated solenoid valve includes a valve body having a main valve orifice 11 and a pilot valve orifice 12. The valve body is formed with an accommodating chamber 13. The pilot valve orifice 12 communicates with the accommodating chamber 13. The opening and closing of the pilot valve orifice 12 guides the opening and closing of the main valve orifice 11. The opening and closing of the main valve orifice 11 realizes the connection and disconnection of a water inlet pipe 14 and a water outlet pipe 15 of the pilot-operated solenoid valve.

The operating structure includes a knob 2, an adjustment rod 3, and a water stop nut 4. The knob 2 is positioned and fitted to an opening of the accommodating chamber 13. The adjustment rod 3 is hermetically fitted in the accommodating chamber 13. A first end of the adjustment rod 3 is threadedly connected to the knob 2, and a second end of the adjustment rod 3 is connected to the water stop nut 4. The adjustment rod 3 is movable along an axial direction of the accommodating chamber 13 with rotation of the knob 2 to drive the water stop nut 4 for opening and closing the pilot valve orifice 12 to control the opening and closing of the main valve orifice 11.

The knob 2 has a protruding portion 21. The protruding portion 21 faces the adjustment rod 3. The protruding portion 21 is formed with a screw hole 211 for the adjustment rod 3 to be screwed therein. The first end of the adjustment rod 3 is screwed in the screw hole 211.

An annular flange 131 protrudes from the opening of the accommodating chamber 13 toward the knob 2. The knob 2 is sleeved on the annular flange 131. The protruding portion 21 is inserted in the annular flange 131 and is positioned by a limiting buckle 5 to restrain the knob 2 from being displaced along the axial direction of the accommodating chamber 13.

The annular flange 131 is formed with an insertion hole 132 for the limiting buckle 5 to be movably fitted therein. The insertion hole 132 passes through the inner wall of the annular flange 131. The outer periphery of the protruding portion 21 is formed with an insertion groove 212 for the limiting buckle 5 to be fitted therein. The limiting buckle 5 is inserted into the insertion hole 132 and fitted in the insertion groove 212 to restrain the knob 2 from moving in the axial direction of the accommodating chamber 13.

The outer periphery of the adjustment rod 3 is formed with a limiting block 31. The side wall of the accommodating chamber 13 is formed with a limiting groove 133. The limiting block 31 is engaged with the liming groove 133 to restrain rotation of the adjustment rod 3 in the accommodating chamber 13, so that the rotation of the knob 2 can only move the adjustment rod 3 along the axial direction of the accommodating chamber 13, thereby driving the water stop nut 4 to move.

At least one sealing ring 6 is sleeved on the outer periphery of the adjustment rod 3. The sealing ring 6 is movably and hermetically fitted between the outer periphery of the adjustment rod 3 and the side wall of the accommodating chamber 13. In this embodiment, the number of the sealing rings 6 is two.

The valve body 1 is provided with a water quality monitoring device 7 for detecting water quality of water passing through the valve body 1 and sending a water quality signal. In this embodiment, the water quality monitoring device 7 is disposed at the outlet end of the valve body 1.

Through the above structure, the knob 2 of the present invention is rotatably fitted at the opening of the accommodating chamber 13. The rotation of the knob 2 drives the adjustment rod 3 to move the water stop nut 4 to open or close the pilot valve orifice 12, so that the rotation of the knob 2 no longer generates displacement, which is convenient for operation and more suitable for the limited space under the basin. In addition, the present invention does not require a complicated mechanical connecting structure, has a simple structure, is easy to install, is more suitable for the improvement of the existing structures, and reducing the cost of improvement.

In addition, the water quality monitoring device 7 can detect the quality of the water source in real time to ensure the health of users.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A pilot-operated solenoid valve including a valve body having a main valve orifice and a pilot valve orifice,
   the valve body being formed with an accommodating chamber, the pilot valve orifice communicating with the accommodating chamber; and
   an operating structure including a knob, an adjustment rod, and a water stop nut; the knob being positioned and fitted to an opening of the accommodating chamber, the adjustment rod being hermetically fitted in the accommodating chamber, a first end of the adjustment rod being threadedly connected to the knob, a second end of the adjustment rod being connected to the water stop nut; the adjustment rod being movable in an axial direction of the accommodating chamber with rotation of the knob to drive the water stop nut for selectively opening and closing the pilot valve orifice,
   wherein the knob has a protruding portion; the protruding portion faces the adjustment rod; the protruding portion is formed with a screw hole for the adjustment rod to be screwed therein; and the first end of the adjustment rod is screwed in the screw hole;
   wherein an annular flange protrudes from the opening of the accommodating chamber toward the knob, the knob is sleeved on the annular flange, and the protruding portion is inserted in the annular flange and is positioned by a limiting buckle;
   wherein the annular flange is formed with an insertion hole for the limiting buckle to be movably fitted therein, the insertion hole passes through an inner wall of the annular flange, an outer periphery of the protruding portion is formed with an insertion groove for the limiting buckle to be fitted therein, the limiting buckle is inserted into the insertion hole and fitted in the insertion groove to restrain the knob from moving in the axial direction of the accommodating chamber; and
   wherein the annular flange that protrudes from the opening of the accommodating chamber is combined with the valve body and the limiting buckle is partially seated in the insertion hole of the annular flange and partially fitted in the insertion groove of the protruding portion of the knob to constrain movement of the knob that is fitted in the opening of the accommodating chamber of the valve body relative to the valve body in the axial direction of the accommodating chamber of the valve body.

2. The pilot-operated solenoid valve as claimed in claim 1, wherein an outer periphery of the adjustment rod is formed with a limiting block, a side wall of the accommodating chamber is formed with a limiting groove, and the limiting block is engaged with the limning groove to restrain rotation of the adjustment rod in the accommodating chamber.

3. The pilot-operated solenoid valve as claimed in claim 1, wherein at least one sealing ring is sleeved on an outer periphery of the adjustment rod, and the sealing ring is movably and hermetically fitted between the outer periphery of the adjustment rod and a side wall of the accommodating chamber.

4. The pilot-operated solenoid valve as claimed in claim 3, wherein the at least one sealing ring includes two sealing rings.

5. The pilot-operated solenoid valve as claimed in claim 1, wherein the valve body is provided with a water quality monitoring device for detecting water quality of water passing through the valve body and sending a water quality signal.

\* \* \* \* \*